US012286572B2

(12) United States Patent
Tse et al.

(10) Patent No.: US 12,286,572 B2
(45) Date of Patent: Apr. 29, 2025

(54) ADHESIVE PRIMERS AND ARTICLES INCLUDING THE SAME

(71) Applicant: Solventum Intellectual Properties Company, Maplewood, MN (US)

(72) Inventors: Kiu-Yuen Tse, Woodbury, MN (US); David T. Amos, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 490 days.

(21) Appl. No.: 17/783,593

(22) PCT Filed: Dec. 17, 2020

(86) PCT No.: PCT/IB2020/062112
§ 371 (c)(1),
(2) Date: Jun. 8, 2022

(87) PCT Pub. No.: WO2021/124200
PCT Pub. Date: Jun. 24, 2021

(65) Prior Publication Data
US 2022/0372345 A1 Nov. 24, 2022

Related U.S. Application Data

(60) Provisional application No. 62/951,570, filed on Dec. 20, 2019.

(51) Int. Cl.
*C09J 7/50* (2018.01)
*A61L 24/04* (2006.01)
(Continued)

(52) U.S. Cl.
CPC ............... *C09J 7/50* (2018.01); *A61L 24/046* (2013.01); *C09J 7/21* (2018.01); *C09J 7/243* (2018.01);
(Continued)

(58) Field of Classification Search
CPC .... A61L 24/046; C09J 7/26; C09J 7/30; C09J 7/243; C09J 7/255; C09J 7/50; C09J 7/21;
(Continued)

(56) References Cited

U.S. PATENT DOCUMENTS 3,645,835 A 2/1972 Hodgson et al.
3,825,379 A 7/1974 Lohkamp et al.
(Continued)

FOREIGN PATENT DOCUMENTS

EP 1228113 B1 * 3/2005 .......... C08F 283/006
EP 2184310 A1 5/2010
(Continued)

OTHER PUBLICATIONS

Billmeyer JR., "Textbook of Polymer Science—Second Edition", (1971), 84-85.
(Continued)

*Primary Examiner* — Carlos N Lopez

(57) ABSTRACT

Provided are adhesive articles that include a silicone adhesive and a substrate, with a primer layer interposed between the silicone adhesive and the substrate. The primer layer includes a polymer having a polyorganosiloxane pendant group P represented by the formula (I) where each $R^1$ is independently an alkyl, haloalkyl, arylalkyl, alkenyl, aryl, or aryl substituted with an alkyl, alkoxy, or halo; R2 is an alkyl or an alkenyl group; R3 is an alkylene or an arylalkylene group; and n is an integer in the range of 1 to 20. The primer layer typically improves the adhesion between the silicone adhesive and a wide variety of substrates.

(Continued)

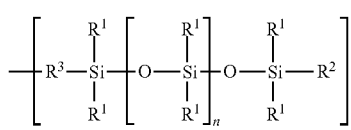

(I)

13 Claims, 1 Drawing Sheet

(51) Int. Cl.
    *C09J 7/21* (2018.01)
    *C09J 7/24* (2018.01)
    *C09J 7/25* (2018.01)
    *C09J 7/26* (2018.01)
    *C09J 7/30* (2018.01)

(52) U.S. Cl.
    CPC ............ *C09J 7/255* (2018.01); *C09J 7/26* (2018.01); *C09J 7/30* (2018.01); *C09J 2301/414* (2020.08); *C09J 2301/416* (2020.08); *C09J 2400/243* (2013.01); *C09J 2400/263* (2013.01); *C09J 2423/046* (2013.01); *C09J 2467/006* (2013.01); *C09J 2475/003* (2013.01); *C09J 2475/006* (2013.01); *C09J 2483/00* (2013.01); *C09J 2483/003* (2013.01)

(58) Field of Classification Search
    CPC .......... C08F 220/1808; C08F 220/1804; C08F 220/14; C08F 230/08; C08F 220/34
    See application file for complete search history.

(56) References Cited

U.S. PATENT DOCUMENTS

| | | |
|---|---|---|
| 3,849,241 A | 11/1974 | Butin et al. |
| 4,595,001 A | 6/1986 | Potter et al. |
| 5,088,483 A | 2/1992 | Heinecke et al. |
| 5,160,315 A | 11/1992 | Heinecke et al. |
| 5,230,701 A | 7/1993 | Meyer et al. |
| 5,238,733 A | 8/1993 | Joseph et al. |
| 5,516,581 A | 5/1996 | Kreckel et al. |
| 5,601,851 A | 2/1997 | Terakawa |
| 7,090,922 B2 | 8/2006 | Zhou et al. |
| 7,897,609 B2* | 3/2011 | Niwas ................. C07D 471/14 546/82 |
| 8,541,481 B2 | 9/2013 | Determan et al. |
| 9,890,302 B2 | 2/2018 | Tse et al. |
| 10,369,247 B2* | 8/2019 | Fung ........................ C09J 7/50 |
| 2008/0233348 A1 | 9/2008 | Ishiwatari et al. |
| 2011/0212325 A1 | 9/2011 | Determan et al. |
| 2012/0070480 A1* | 3/2012 | Amos .................... A61L 15/46 514/159 |
| 2014/0287642 A1* | 9/2014 | Kumar ................... B32B 5/024 526/279 |
| 2014/0349108 A1* | 11/2014 | Fung ........................ C09J 7/50 428/355 R |
| 2015/0165087 A1* | 6/2015 | Fung ....................... C08L 83/00 604/500 |
| 2016/0230019 A1 | 8/2016 | Yao et al. |
| 2017/0362470 A1 | 12/2017 | Kluge et al. |

FOREIGN PATENT DOCUMENTS

| | | |
|---|---|---|
| JP | 2001081393 A | 3/2001 |
| WO | 1995006691 A1 | 3/1995 |
| WO | 1997002375 A1 | 1/1997 |
| WO | 2009156608 A2 | 12/2009 |
| WO | WO-2013096530 A1 * 6/2013 ......... A61F 13/0253 |

OTHER PUBLICATIONS

International Search Report for PCT International Application No. PCT/IB2020/062112, mailed on Apr. 14, 2021, 4 pages.

Wente, "Manufacture of Superfine Organic Fibers" Naval Research Laboratories Report No. 4364 (111437), May 1954, 19 pages.

Wente, "Superfine Thermoplastic Fibers" Industrial & Engineering Chemistry, Aug. 1956, vol. 48, No. 8, pp. 1342-1346.

* cited by examiner

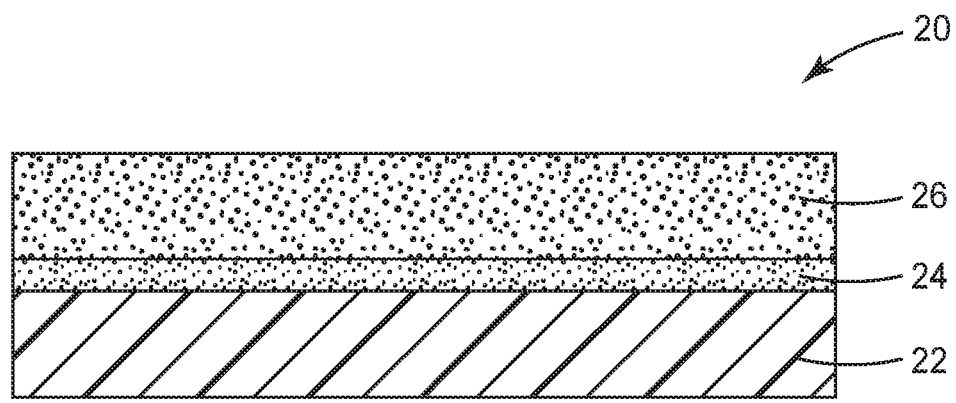

ADHESIVE PRIMERS AND ARTICLES INCLUDING THE SAME

CROSS REFERENCE TO RELATED APPLICATIONS

This application is a national stage filing under 35 U.S.C. 371 of PCT/2020/062112, filed Dec. 17, 2020, which claims the benefit of Provisional Application No. 62/951,570, filed Dec. 20, 2019, the disclosure of which is incorporated by reference in its/their entirety herein.

TECHNICAL FIELD

The present disclosure relates generally to the field of adhesive primers and particularly to adhesive primers for use in articles having a silicone adhesive layer.

BACKGROUND

Silicone adhesives, including silicone pressure sensitive adhesives, may have a variety of desirable properties. In various applications, silicone adhesives may exhibit, for example, good adhesion over a wide temperature range, resistance to environmental factors such as oxidation and ultraviolet light, high moisture vapor transmission rates, and good electrical properties. Certain silicone adhesives are useful for medical tapes and dressings because the silicone adhesive can provide adhesion when desired but can also be readily removed from the skin without causing trauma by stripping skin cells and/or hair.

SUMMARY

The present disclosure provides adhesive articles that include a silicone adhesive and a substrate, with a primer layer interposed between the silicone adhesive and the substrate. The primer layer includes a polymer having a polyorganosiloxane pendant group P represented by the formula

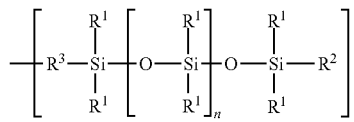

where each $R^1$ is independently an alkyl, haloalkyl, arylalkyl, alkenyl, aryl, or aryl substituted with an alkyl, alkoxy, or halo; R2 is an alkyl or an alkenyl group; R3 is an alkylene or an arylalkylene group; and n is an integer in the range of 1 to 20. The primer layer typically improves the adhesion between the silicone adhesive and a wide variety of substrates. The adhesion is improved even though the disclosed primer layer does not contain reactive functional groups that can bond with the substrate and/or the silicone adhesive. The primer layer in the articles disclosed herein may be more effective than other primers for improving the adhesion between the substrate and the silicone adhesive.

In one aspect, the present disclosure provides an adhesive article that includes a substrate, a primer layer disposed on the substrate, wherein the primer layer includes a polymer having a polyorganosiloxane pendant group P, and a silicone adhesive disposed on the primer layer.

In another aspect, the present disclosure provides a method of making such an adhesive article. The method includes coating the primer layer onto the substrate, coating a silicone adhesive composition onto the primer layer, and crosslinking the silicone adhesive composition to form the silicone adhesive. In some embodiments, crosslinking comprises exposing the silicon adhesive composition to radiation to form a radiation crosslinked silicone adhesive. In some of these embodiments, radiation includes at least one of electron-beam or gamma radiation.

In another aspect, the present disclosure provides a method of making such an adhesive article. The method includes coating the primer layer onto the substrate, coating a silicone adhesive composition onto a release liner, crosslinking the silicone adhesive composition to form the silicone adhesive, and laminating the silicone adhesive to the primer layer. In some embodiments, crosslinking comprises exposing the silicon adhesive composition to radiation to form a radiation crosslinked silicone adhesive. In some of these embodiments, radiation includes at least one of electron-beam or gamma radiation In this disclosure, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

"Alkyl", "alkenyl", and the prefix "alk-" are inclusive of both straight chain and branched chain alkyl groups. Alkyl and alkenyl groups can have up to 30 carbons (in some embodiments, up to 20, 15, 12, 10, 8, 7, 6, or 5 carbons) unless otherwise specified.

"Cycloalkyl" includes monocyclic or polycyclic groups having from 3 to 10 (in some embodiments, 3 to 6 or 5 to 6) ring carbon atoms.

"Alkylene" refers to a multivalent (e.g., divalent) form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

The term "(meth)acrylate" refers to monomeric acrylic or methacrylic esters of alcohols. Acrylate and methacrylate monomers are referred to collectively herein as "(meth)acrylates". Polymers described as being "(meth)acrylate-based" are polymers or copolymers prepared primarily (greater than 50% by weight (wt. %), greater than 60 wt. %, greater than 70 wt. %, greater than 80 wt. %, greater than 90 wt. %, greater than 95 wt. %, or 100 wt. %) from (meth) acrylate monomers and may include additional ethylenically unsaturated monomers such as various (meth)acrylamide monomers or various vinyl monomers that do not have a (meth)acryloyl group.

The term "polyurethane" as used herein includes compounds having more than one carbamate and/or urea group and can also contain biuret, allophanate, uretdione, or isocyanurate linkages in any combination.

The term "pressure sensitive adhesive" as used herein refer to adhesives that possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power.

Number average molecular weights can be measured, for example, by gel permeation chromatography (i.e., size exclusion chromatography) or by nuclear magnetic resonance spectroscopy using techniques known in the art.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure. Features and advantages of the present disclosure will be further understood upon consideration of the detailed description as well as the appended claims.

BRIEF DESCRIPTION OF THE DRAWINGS

FIG. 1 is a schematic side view of an embodiment of an adhesive article according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The FIGURES may not be drawn to scale.

DETAILED DESCRIPTION

In certain silicone adhesive tapes, delamination of the silicone adhesive from the tape backing can be a problem. Such delamination can make it difficult to remove the adhesive from skin, for example, and may limit the ability to reuse the tape. Provided in the present disclosure are adhesive articles that include a silicone adhesive and a substrate, with a primer layer interposed between the silicone adhesive and the substrate, where the primer layer includes a polymer having a polyorganosiloxane pendant group P represented by the formula

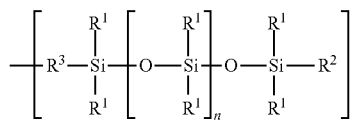

where each $R^1$ is independently an alkyl, haloalkyl, arylalkyl, alkenyl, aryl, or aryl substituted with an alkyl, alkoxy, or halo; R2 is an alkyl or an alkenyl group; R3 is an alkylene or an arylalkylene group; and n is an integer in the range of 1 to 20. The primer layer typically improves the adhesion between the silicone adhesive and a wide variety of substrates, thus preventing delamination of the silicone adhesive from the tape backing when the adhesive is removed from skin, for example, and allowing for reuse of the tape.

FIG. 1 is a schematic side view of an embodiment of an adhesive article 20. In adhesive article 20, primer layer 24 is disposed on substrate 22. Silicone adhesive 26 is disposed on the primer layer 24. It should be understood that each of the substrate 22, primer layer 24, and silicone adhesive 26 are distinct elements of adhesive article 20. Though not shown, in some embodiments, the primer layer 24 may, at least partially, interpenetrate with the substrate 22.

Primer Layer

The primer layer 24 in the adhesive article according to and/or made according to the present disclosure includes a polymer having a polyorganosiloxane pendant group P represented by the formula

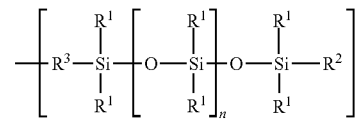

where each $R^1$ is independently an alkyl, haloalkyl, arylalkyl, alkenyl, aryl, or aryl substituted with an alkyl, alkoxy, or halo; $R^2$ is an alkyl or an alkenyl group; R3 is an alkylene or an arylalkylene group; and n is an integer in the range of 1 to 20.

Suitable alkyl groups for $R^1$ and $R^2$ in pendant group P have, in some embodiments, 1 to 10, 1 to 6, or 1 to 4 carbon atoms. Exemplary alkyl groups $R^1$ and $R^2$ in pendant group P include methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halogen atoms and 3 to 10 carbon atoms. Suitable alkenyl groups for $R^1$ and $R^2$ have, in some embodiments, 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable arylalkylenyl groups for $R^1$ usually have an alkylene group with 1 to 10 carbon atoms and an aryl group with 6 to 12 carbon atoms. In some exemplary arylalkylenyl groups, the aryl group is phenyl and the alkylene group has 1 to 10 carbon atoms, 1 to 6 carbon atoms, or 1 to 4 carbon atoms (i.e., the structure of the arylalkylenyl is alkylene-phenyl where an alkylene is bonded to a phenyl group).

In pendant group P, $R^3$ is an alkylene or an arylalkylene. Suitable alkylenes often have 2 to 10, 2 to 6, or 2 to 4 carbon atoms. Exemplary alkylene groups include ethylene, propylene, and butylene. In some embodiments, $R^3$ is ethylene. Suitable arylalkylene groups usually contain an arylene group having 6 to 12 carbon atoms bonded to an alkylene group having 1 to 10 carbon atoms. Some exemplary arylalkylene groups are phenylene-alkylene and alkylene-phenylene where the phenylene is bonded to an alkylene having 1 to 10 carbon atoms, 1 to 8 carbon atoms, 1 to 6 carbon atoms, or 1 to 4 carbon atoms.

The subscript n in pendant group P is an integer in a range from 1 to 20. For example, the value of n can be up to 18, up to 16, up to 14, up to 12, up to 10, up to 8, up to 6, or up to 4. In some embodiments, the value of n is in the range of 1 to 18, 1 to 16, 1 to 14, 1 to 12, 1 to 10, 1 to 8, 1 to 6, or 1 to 4.

In some embodiments, the polymer having a polyorganosiloxane pendant group P useful for practicing the present disclosure may be a (meth)acrylate polymer. Such (meth)acrylate polymers having a polyorganosiloxane pendant group P useful for practicing the present disclosure may be prepared by methods known in the art, for example, by reacting a silicone acrylate (e.g., such as those available, for example, from Shin-Etsu Silicone, Akron, OH, under the trade designation "KF-2012") with one or more acrylate monomers (e.g., methyl methacrylate, iso-octyl acrylate, tert-butyl amino ethyl methacrylate) in the presence of a polymerization initiator (e.g., 2,2'-Azobis(2-methylbutyronitrile), obtained under the trade designation "VAZO-67" from DuPont, Wilmington, DE) at an elevated temperature.

In some embodiments, the (meth)acrylate polymer comprises 2 wt. % to 40 wt. %, optionally 5 wt. % to 20 wt % (e.g., 10 wt. %) of a first (meth)acrylate monomer represented by the formula

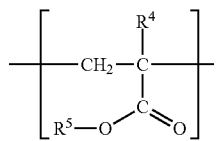

where $R^4$ is hydrogen or methyl, and $R^5$ is pendant group P. In some embodiments, the (meth)acrylate polymer further comprises 10 wt. % to 98 wt. %, optionally 30 wt. % to 85 wt % (e.g., 40 wt. %) of a second (meth)acrylate monomer represented by the formula

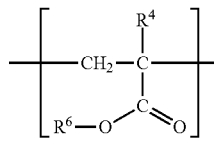

where $R^4$ is hydrogen or methyl, and $R^6$ is an alkyl group having 1 to 12 (e.g., 3 to 12) carbon atoms. In some embodiments, the (meth)acrylate polymer further comprises 10 wt. % to 88 wt. %, optionally 30 wt. % to 70 wt % (e.g., 40 wt. %) of a third (meth)acrylate monomer represented by the formula

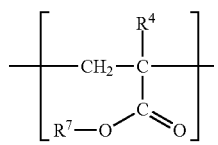

where $R^4$ is hydrogen or methyl, and $R^7$ is an alkyl group different from $R^6$ and having 1 to 12 (e.g., 3 to 12) carbon atoms. In some embodiments, the (meth)acrylate polymer further comprises 1 wt. % to 15 wt. %, optionally 2 wt. % to 14 wt % (e.g., 10 wt. %) of a fourth (meth)acrylate monomer represented by the formula

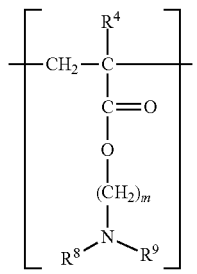

where $R^4$ is hydrogen or methyl, $R^8$ is an alkyl group having 1 to 4 carbon atoms, $R^9$ is hydrogen or an alkyl group having 1 to 4 carbon atoms, and m is an integer in the range of 2 to 6 (e.g., 2 to 3).

The (meth)acrylate polymers having a polyorganosiloxane pendant group P may have a variety of number average molecular weights. For example, a (meth)acrylate polymer having a polyorganosiloxane pendant group P having a weight average molecular weight of at least 50,000 grams per mole (in some embodiments, at least 60,000, 70,000, or 80,000 grams per mole) may be useful. In some embodiments, the (meth)acrylate polymer having a polyorganosiloxane pendant group P has a weight average molecular weight of up to 500,000 grams per mole (in some embodiments, up to 400,000 or 300,000 grams per mole). Useful weight average molecular weights for the (meth)acrylate polymer having a polyorganosiloxane pendant group P may be, for example, in a range from 50,000 grams per mole to 500,000 grams per mole, 60,000 grams per mole to 400,000 grams per mole, or 70,000 grams per mole to 300,000 grams per mole.

In some embodiments, the polymer having a polyorganosiloxane pendant group P useful for practicing the present disclosure may be a polyurethane polymer. Such polyurethane polymers having a polyorganosiloxane pendant group P useful for practicing the present disclosure may be prepared by methods known in the art, for example, by reacting a silicone diol with a polyisocyanate at an elevated temperature. The resulting isocyanate-terminated prepolymer solution can then be treated with a diamine such as an alkylene diamine, another silicone diamine, an arylene diamine, an alkylarylene diamine, an arylalkylene diamine, or a polyoxyalkylene diamine (e.g., such as those available, for example, from Huntsman, The Woodlands, Tex., under the trade designation "JEFFAMINE".

Polyurethane polymers having a polyorganosiloxane pendant group P of the present disclosure commonly include 2 wt. % to 30 wt. % (e.g., 5 wt. % to 20 wt. %) of the silicone diol, 8 wt. % to 30 wt. % (e.g., 15 wt. % to 25 wt. %) of the polyisocyanate, and 10 wt. % to 90 wt. % (e.g., 50 wt. % to 80 wt. %) of an —OH or amine terminated polyol.

The silicone diol component may be a polyether (e.g., PEG, PPG, PolyTHF), a polyester polyol, polycarbonate polyols, an amine terminated polyethers, or combinations thereof. Suitable silicone diols are commercially available, for example, from Shin-Etsu Chemical Company, Tokyo, Japan, under the trade designation "X-22-176DX".

The polyisocyanate component may comprise various polyfunctional isocyanate compounds. Examples of such polyfunctional isocyanate compounds include polyfunctional aliphatic isocyanate compounds, polyfunctional aliphatic cyclic isocyanate compounds, and a polyfunctional aromatic isocyanate compounds. Examples of the polyfunctional aliphatic isocyanate compounds include trimethylene diisocyanate, tetramethylene diisocyanate, hexamethylene diisocyanate, pentamethylene diisocyanate, 1,2-propylene diisocyanate, 1,3-butylene diisocyanate, dodecamethylene diisocyanate, and 2,4,4-trimethylhexamethylene diisocyanate. Examples of the polyfunctional aliphatic cyclic isocyanate compounds include 1,3-cyclopentene diisocyanate, 1,3-cyclohexane diisocyanate, 1,4-cyclohexane diisocyanate, isophorone diisocyanate, hydrogenated diphenylmethane diisocyanate, hydrogenated xylylene diisocyanate, hydrogenated tolylene diisocyanate, hydrogenated tetramethylxylene diisocyanate, and bio-based polyfunctional aliphatic cyclic isocyanates, such as 2-heptyl-3,4-bis(9-isocyanatononyl)-1-pentylcyclohexane available under trade designation "DDI 1410" from BASF, Ludwigshafen, Germany.

Examples of the polyfunctional aromatic isocyanate compounds include phenylene diisocyanate, 2,4-tolylene diisocyanate, 2,6-tolylene diisocyanate, 2,2'-diphenylmethane diisocyanate, 4,4' diphenylmethane diisocyanate, 4,4'-toluidine diisocyanate, 4,4'-diphenyl ether diisocyanate, 4,4'-diphenyl diisocyanate, 1,5-naphthalene diisocyanate, and xylylene diisocyanate.

In some embodiments, the polyurethane polymer having a polyorganosiloxane pendant group P comprises 10 wt. % to 30 wt. %, optionally 15 wt. % to 25 wt % (e.g., 18 wt. %) of a first monomer represented by the formula

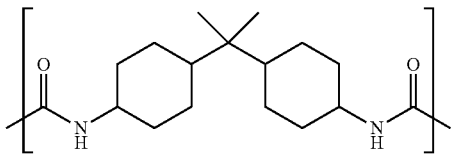

60 wt. % to 85 wt. % (e.g., 72 wt. %) of a second monomer represented by the formula

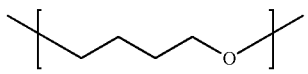

and 2 wt. % to 30 wt. %, optionally 5 wt. % to 20 wt % (e.g., 10 wt. %) of a third monomer represented by the formula

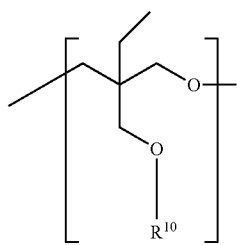

wherein $R^{10}$ is pendant group P.

The polyurethane polymers having a polyorganosiloxane pendant group P may have a variety of number average molecular weights. For example, a polyurethane polymer having a polyorganosiloxane pendant group P having a weight average molecular weight of at least 10,000 grams per mole (in some embodiments, at least 12,000, 15,000, or 20,000 grams per mole) may be useful. In some embodiments, the polyurethane polymer having a polyorganosiloxane pendant group P has a weight average molecular weight of up to 100,000 grams per mole (in some embodiments, up to 75,000, or 50,000 grams per mole). Useful weight average molecular weights for the polyurethane polymer having a polyorganosiloxane pendant group P may be, for example, in a range from 10,000 grams per mole to 100,000 grams per mole, 15,000 grams per mole to 75,000 grams per mole, or 20,000 grams per mole to 50,000 grams per mole.

In some embodiments, the primer layer cannot be considered a pressure sensitive adhesive as defined above. In some embodiments, the primer layer is substantially free of tackifier, including any of the tackifiers described below. "Substantially free of tackifier" can mean that the primer layer includes a tackifier but in an amount that is insufficient to make the primer layer tacky at room temperature. In some embodiments, "substantially free of tackifier" refers to having up to 10, 5, 2, or 1 percent tackifier by weight, based on the total weight of the primer layer. "Substantially free of tackifier" includes being free of tackifier (that is, having no tackifier present).

Substrate

The substrate 22, also referred to herein as a "backing," may be any useful material known to those of skill in the art and can include single-layer and multi-layer constructions. In some embodiments, substrates of the present disclosure can include medical backings that are particularly suitable for use in medical articles, i.e., having have the proper breathable, optical, and mechanical properties. Generally, the substrate will be composed of a flexible material to facilitate application of the adhesive article around curves and bends in the body, such as fingers, elbows or knees. In addition, the substrate may optionally be breathable. The substrate may also provide an impermeable barrier to the passage of liquids and at least some gases. Examples of suitable substrates include but are not limited to: woven and nonwoven fibrous webs, knit, films, fabrics, foams, polymeric films, or combinations thereof. In some embodiments, the substrates may be a thermoplastic substrate, a paper substrate, a woven substrate, a nonwoven substrate, or combinations thereof. In some embodiments, the thermoplastic is a polyolefin, a polyester, a polyurethane, or an ethylene-vinyl acetate copolymer. In some embodiments, a transparent substrate is desirable to allow for viewing of the underlying skin or medical device.

Wovens can be made of natural or synthetic fibers, including, but not limited to cotton, nylon, polyester, polyurethanes, polyimides, polyamides, cloth or acrylic-based materials. An example of a woven substrate includes, but is not limited to, a polyethylene terephthalate ("PET")/Spandex woven blend. In one embodiment, the woven may be a 70% PET/30% Spandex woven blend. In other embodiments, the woven may be comprised of 95% PET/5% Spandex. In yet another embodiment, the woven can be comprised of 100% PET.

Suitable nonwoven backings can be formed of a variety of materials, including, but not limited to: polyesters, polyurethanes, polyimides, polyamides, polystyrenes, cellulose, polyolefins, glass fibers, ceramic fibers, and combinations thereof. An example of a suitable nonwoven backing layer material is a high-strength nonwoven fabric available from Jacob Holm, Basel Switzerland under the trademark SONTARA, including SONTARA 8010, a hydroengangled polyester fabric. Other suitable nonwoven webs include a hydroentangled polyester fabric available from Veratec, a division of International Paper of Walpole, Mass. Another suitable nonwoven web is the nonwoven elastomeric web described in U.S. Pat. No. 5,230,701, herein incorporated by reference in its entirety.

Other suitable non-wovens could have fibers entangled with each other in the form of a coherent breathable fibrous nonwoven substrate. Suitable nonwoven backing layers can be formed as melt blown microfiber webs using the apparatus discussed, for example, in Wente, Van A., "Superfine Thermoplastic Fibers", Industrial Engineering Chemistry, Vol. 48, pages 1342-1346, Wente, Van A. et al., "Manufacture of Superfine Organic Fibers", Report No. 4364 of the Navel Research Laboratories, published May 25, 1954, and in U.S. Pat. Nos. 3,849,241; 3,825,379; and others. Conjugate melt blown fibers can be formed, for example, as a multilayer fiber as described, for example, in U.S. Pat. Nos. 5,238,733; 5,601,851; or PCT Publication No. WO 97/2375. Multilayered and sheath-core melt blown fibers are described, for example, in U.S. Pat. No. 5,238,733, the substance of which is incorporated herein by reference. Another suitable nonwoven substrate may include COTRAN 9700, a melt-blown polyurethane nonwoven backing, available from 3M Company, St. Paul, MN.

The substrate may also be comprised of foam. Potentially useful polymeric backing materials are disclosed in U.S. Pat. No. 5,516,581 (Kreckel et al.) and PCT Publication No. WO 95/06691.

Representative examples of potentially useful polymeric backing materials for polymeric foam layers or polymeric film layers include, but are not limited to, polyurethanes; polyesters, e.g., polyethylene terephthalate ("PET"); polyolefins, e.g., polyethylene, including high density polyethylene, low density polyethylene, linear low density polyethylene, and linear ultra-low density polyethylene, polypropylene, polybutylenes, or combinations thereof (e.g., a polyethylene blend); vinyl copolymers, e.g., polyvinyl chlorides, both plasticized and unplasticized, polyvinyl acetates, or combinations thereof; polyimides; polyamides; polystyrenes; cellulose acetate; olefin copolymers, e.g., ethylene/methacrylate copolymers, ethylene/vinylacetate copolymers, acrylonitrile-butadiene-styrene copolymers, ethylene/propylene copolymers, or combinations thereof; acrylic polymers and copolymers; and combinations thereof. Mixtures or blends of a plastic or plastic and elastomer materials, such as polypropylene/polyethylene, polyurethane/polyolefin, polyurethane/polycarbonate, and polyurethane/polyester, can also be used. Suitable films can also include metallic foils.

Films may be used to increase load bearing strength and rupture strength of the adhesive article. Films are particularly well suited to applications involving adhering smooth surfaces together. A film substraate, or layer thereof, can have a thickness of about 10 micrometers (0.4 mil) to about 254 micrometers (10 mils). Films can be continuous or perforated.

The substrate can be translucent or transparent polymeric elastic films, and can include, but is not limited to: films formed of elastomeric polyurethanes, co-polyesters (e.g., ARNITEL 3108 from Koninklijke DSM N. V., Heerlen, Netherlands), polyethylenes, or combinations thereof. In some embodiments, the substrate has high moisture vapor permeability, but is generally impermeable to liquid water so that microbes and other contaminants are sealed out from the area under the substrate. One example of a suitable material is a high moisture vapor permeable film such as described in U.S. Pat. Nos. 3,645,835 and 4,595,001, the disclosures of which are herein incorporated by reference in their entireties. In high moisture vapor permeable film/adhesive composites, the composite should transmit moisture vapor at a rate equal to or greater than human skin such as, for example, at a rate of at least 300 g/m$^2$/24 hrs at 37° C./100-10% RH, or at least 700 g/m$^2$/24 hrs at 37° C./100-10% RH, or at least 2000 g/m$^2$/24 hrs at 37° C./100-10% RH using the inverted cup method as described in U.S. Pat. No. 4,595,001. Perforated substrates or films or pattern coated adhesives may be used to increase the moisture vapor transmission. In some embodiments, the substrate is an elastomeric polyurethane, polyester (e.g., HOSTAPHAN 3SAB from Mitsubishi Polyester Film, Greer, SC), or polyether block amide films. These films combine the desirable properties of resiliency, elasticity, high moisture vapor permeability, and transparency. A description of this characteristic of backing layers can be found in issued U.S. Pat. Nos. 5,088,483 and 5,160,315, the disclosures of which are hereby incorporated by reference.

Commercially available examples of potentially suitable substrate materials may include the thin polymeric film backings sold under the trade names TEGADERM (3M Company), OPSITE (Smith & Nephew), etc. Many other backing layers may also be used, including those commonly used in the manufacture of surgical incise drapes (e.g., incise drapes manufactured by 3M Company under the trade names STERIDRAPE and IOBAN), etc.

In some embodiments, it may be desirable that the substrate be kept relatively thin to, for example, improve conformability. For example, the backing layer may be formed of polymeric films with a thickness of 200 micrometers or less, or 100 micrometers or less, potentially 50 micrometers or less, or even 25 micrometers or less.

Silicone Adhesive

"Adhesion" or ("adhesion strength") refers to the force required to separate an adhesive from an underlying substrate. Adhesion can be measured in a number of ways. For example, adhesion can be defined by peel force or shear force. In some embodiments, adhesion can be defined by peel adhesion as described below in the Adhesive Anchorage Test, which measures the strength of a bond between a primed substrate and a cured adhesive. A primer is considered to be successful if this bond has sufficient strength so that the adhesive is not removed from the primed substrate when the adhesive is removed from a surface to which it had been adhered.

Adhesion is highly dependent on the specific substrate being adhered to, as well as the time the adhesive (e.g., pressure sensitive adhesive) is allowed to dwell on the substrate. The peel adhesion to biological substrates such as human skin is known to be highly variable. Skin type, location on the body, and other factors can affect results. Generally, average values of peel adhesion from skin are subject to large standard deviations. In some embodiments, the average peel adhesion for human skin may be less than about 300 gram/2.54 cm, particularly less than about 200 gram/2.54 cm, and more particularly, less than about 100 gram/2.54 cm.

Suitable adhesives for use in some embodiments of the present disclosure include silicone adhesives that provide acceptable adhesion to skin and are acceptable for use on skin (e.g., the adhesive should preferably be non-irritating and non-sensitizing). One problem with using adhesive articles for medical applications is that the removal of the adhesive article can cause trauma to the skin. This is particularly troublesome in patients with sensitive skin, such as infants and the elderly, and can become severe with chronic patients where adhesive articles are repeatedly attached and removed over a long-term period.

The widespread use of adhesives in medical applications has led to the development of adhesives and adhesive articles that are gentle to the skin that do not strip off skin cells significantly when removed. Generally, silicone adhesives are able to effectively secure dressings and tape to skin and upon removal from the skin, produce little or no skin damage. In some embodiments, the silicone adhesive of the present disclosure is a pressure sensitive adhesive ("PSA") that can adhere the substrate to skin with application of light pressure and without the need for heat or other external sources to active adhesion. In other embodiments, the silicone adhesive is a gel.

Pressure sensitive adhesives are well known to one of ordinary skill in the art to possess certain properties at room temperature including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as pressure sensitive adhesives are polymers designed and formulated to exhibit the requisite viscoelastic properties resulting in a desired balance of tack, peel adhesion, and shear strength. The most commonly used polymers for preparation of pressure sensitive adhesives are natural rubber, synthetic rubbers (e.g., styrene/butadiene copolymers (SBR) and styrene/isoprene/styrene (SIS) block copolymers), various (meth)acrylate (e.g., acrylate and methacrylate) copolymers, and silicones.

The application of pressure sensitive adhesives, including silicone pressure sensitive adhesives, for adhering to skin is known in the art and many examples are commercially available. However, some pressure sensitive adhesives have issues that limit their use for adhesion to skin. For instance, skin damage may result during the removal of a pressure sensitive adhesive that exhibits surface adhesion to skin that is too high. Alternatively, if the surface adhesion to skin is reduced, the pressure sensitive adhesive may lack sufficient holding power to be useful. Additionally, some pressure sensitive adhesives that are relatively rigid or non-conformable compared to skin typically result in considerable patient discomfort during use. Also, even adhesives that have a measured low peel adhesion to skin may cause discomfort during removal, e.g., if the adhesive becomes surface attached around hair.

Another class of adhesives used in medical applications are silicone gels. As used herein, the terms "siloxane" and "silicone" are used interchangeably. The term siloxane is replacing silicone in common usage, but both terms are used in the art. Silicone gel (crosslinked poly dimethylsiloxane ("PDMS")) materials have been used for dielectric fillers, vibration dampers, and medical therapies for promoting scar tissue healing. Commercially available silicone gels are soft, tacky, elastic materials that comprise relatively high levels of fluids (liquids). Silicone gels are typically softer than silicone pressure sensitive adhesives, resulting in less discomfort when adhered to and removed from skin. The combination of low skin trauma upon removal and low skin irritation upon wearing, make silicone gels suitable for gentle to skin adhesive applications.

Examples of commercially available silicone gel adhesive systems include products marketed with the trade names: Dow Corning MG 7-9850; WACKER 2130, BLUESTAR 4317 and 4320, and NUSIL 6345 and 6350. These gentle to the skin adhesives are formed by an addition cure reaction between vinyl-terminated PDMS and hydrogen terminated PDMS, in the presence of a hydrosilylation catalyst (e.g., platinum complex). Vinyl-containing and hydrogen-containing PDMS chains are referred to as 'functionalized' silicones due to their specific curable chemical moieties. Individually, such functional silicones are generally not reactive; however, together they form a reactive silicone system. Generally, due to processing requirements such as the need to be solventless, the desired formulation lifetime, and the reaction kinetics of the curing reactions, these reactive siloxane systems typically use functional PDMS fluids with low viscosities and thus low molecular weights. Additionally, silicone resins (tackifiers sometimes referred to as "silicate resins") and PDMS with multiple hydrogen functionalities (crosslinkers) can be formulated to modify the adhesive properties of the gel.

Pressure sensitive adhesives are used in medical applications because they can have good adhesion to a wide variety of substrates (for example, to skin as well as to tubing, drapes, tape backings, and the like). They can, however, on occasion cause skin damage. Gel adhesives, on the other hand, can have desired low skin trauma. They can, however, have low adhesion, both to skin and to other substrates such as tubing, drapes, tape backings, and the like. Thus, the need remains for adhesives suitable for medical uses that have high adhesion to a wide range of substrates without causing skin damage.

As used herein, the term "gel adhesive" refers to a tacky semi-solid crosslinked matrix containing a liquid or a fluid that is capable of adhering to one or more substrates. The gel adhesives may have some properties in common with pressure sensitive adhesives, but they are not pressure sensitive adhesives.

The term "silicone" or "silicone-based" as used herein refers to polymers that contain units with dialkyl or diaryl siloxane ($—SiR_2O—$) repeating units. The silicone-based polymers may be segmented copolymers or polysiloxanes polymers. The terms silicone and siloxane are used interchangeably.

Silicone adhesives useful for practicing the present disclosure may include, but are not limited to, silicone gel adhesives or silicone pressure sensitive adhesives. Some silicone pressure sensitive adhesive compositions useful for practicing the present disclosure are commercially available, for example, from Dow Corning, Midland, MI, under the trade designation "7735" and from Momentive Performance Materials, Columbus, OH, under the trade designation "SIL-GRIP 6574". Suitable silicone adhesives for medical applications include lightly crosslinked silicone gel adhesives that are soft, tacky, elastic materials with moderate adhesive strength. Silicone gel adhesives typically have excellent wetting characteristics due to their inherent low glass transition temperature, low surface energy, and relatively low storage modulus. The inertness and lack of reactivity of the silicone materials make silicone gels suitable for gentle-to-skin adhesive applications. Additionally, the elastic nature of the crosslinked gel and lack of interaction with hair surfaces debond the adhesives from skin by stretch releasing and further reduces the instances of pain during removal. Some silicone adhesives (e.g., silicone gel adhesives) useful for practicing the present disclosure are commercially available, for example, from Dow Corning under the trade designations "MG 7-9900" and "MG 7-1010"; from Wacker Chemie AG, Munich, Germany, under the trade designation "SIL-PURAN 2130"; from Bluestar Silicones, East Brunswick, NJ, under the trade designations "RT GEL 4317 and "SIL-BIONE RT GEL 4320"; and from NuSIL Silicone Technology, Carpinteria, CA, under the trade designations "MED-6345" and "MED-6350".

In some embodiments, silicone adhesives useful for practicing the present disclosure are formed by an addition cure reaction between vinyl-terminated poly(dimethylsiloxane) (PDMS) and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Additionally, silicate resin tackifiers, such as those described in further detail below, and PDMS with multiple hydrogen functionalities (crosslinkers) can be formulated to modify the adhesive properties of the silicone adhesives. Silicone adhesives resulting from this addition reaction are typically called silicone gel adhesives if they are very lightly crosslinked polydimethysiloxane (PDMS) networks with some level of free (not crosslinked) PDMS fluid and no or low levels of tackifiying resin. By contrast, silicone pressure sensitive adhesives are typically formulated with higher levels of tackifying resins (e.g., 45-60 weight percent). The amount of tackifying resin and control of crosslink density (the chain length of the polymer between the crosslinks) are features that are carefully controlled in silicone adhesives useful for medical articles that will adhere to skin. Silicone adhesives (e.g., silicone gel adhesives) useful for practicing the present disclosure may also include hydroxyl functional groups. Examples of such adhesives are disclosed in Int. Pat. App. Pub. No. WO 2005/102403 (Gantner et al.).

In some embodiments, the silicone adhesive is a radiation crosslinked silicone adhesive, such as those disclosed in U.S. Pat. App. Pub. No. 2011/0212325 (Determan et al.), the disclosure of which is herein incorporated by reference. Radiation crosslinking processes typically require less space and less capital equipment than catalyzed thermal curing processes. Also, radiation crosslinking is typically a faster process than thermal curing, which results in higher throughput and lower manufacturing costs. Radiation curing is typically accomplished through high energy radiation, such as electron beam or gamma ray radiation, as described in U.S. Pat. App. Pub. No. 2011/0212325 (Determan et al.). Reactive functional groups are not required in the adhesive compositions in order to make radiation crosslinked silicone adhesives.

In some embodiments, silicone adhesives useful in the articles and methods of the present disclosure may be prepared by combining one or more poly diorganosiloxane materials (e.g., silicone oils or fluids), optionally with an appropriate tackifying resin, coating the resulting adhesive composition on the substrate or primer, and crosslinking the adhesive composition to form the silicone adhesive. In some embodiments, coating the silicone adhesive composition includes pattern coating. Generally, any known additives useful in the formulation of adhesives may also be included. For example, the adhesive component may contain tackifiers, plasticizers, rheology modifiers as well as active components including for example an antimicrobial agent.

If included, generally, any known tackifying resin may be used. Suitable silicate tackifying resins are commercially available from sources such as Momentive Performance Materials (e.g., under the trade designations "SR545" and "SR1000"), and Wacker Chemie AG (e.g., under the trade designation "MQ 803 TF").

The polysiloxane material, the tackifying resin, if present, and any optional additives (e.g., fillers, pigments, additives for improving adhesion, pharmaceutical agents, cosmetic agents, natural extracts, silicone waxes, and rheology modifiers) may be combined by any of a wide variety of known means prior to being coated and cured. For example, in some embodiments, the various components may be pre-blended using common equipment such as mixers, blenders, mills, and extruders.

In certain embodiments, the silicone adhesive may have a relatively high moisture vapor transmission rate to allow for moisture evaporation. For an adhesive in contact with skin, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348, the disclosures of which are herein incorporated by reference.

The thickness of the silicone adhesive is not particularly limited. In one embodiment, the thickness will be at least about 10 microns, and in some embodiments, at least about 20 microns. In some embodiments, the thickness will be no greater than about 400 microns, and in some embodiments, no greater than about 200 microns.

Adhesive Articles and Methods of Making Adhesive Articles

In some embodiments, an adhesive article 20 of the present disclosure may be part of a medical article. Generally, "medical articles" include, but are not limited to: medical tapes, surgical drapes, medical dressings (e.g., intravenous dressings, wound dressings), electrodes, ostomy pouches, transdermal drug delivery devices (e.g., patches), bandages, and combinations thereof.

In some embodiments, the adhesive article is suitable for application to skin. Therefore, the adhesive article 20 can be a medical tape, bandage, or wound dressing. In some embodiments, the adhesive article can be an IV site dressings, a buccal patch, or a transdermal patch. In some embodiments, the adhesive articles according to the present disclosure may be adhered to the skin of humans and/or animals. The adhesive articles according to the present disclosure may include other materials such as polymeric materials, plastics, natural macromolecular materials (e.g., collagen, wood, cork, and leather), paper, films, foams, woven cloth and non-woven cloth, composites, and combinations of these materials.

In some embodiments, the present disclosure provides a method of making an adhesive article. The method includes coating a primer layer onto a substrate, coating a silicone adhesive composition onto the primer layer, and crosslinking the silicone adhesive composition to form the silicone adhesive. In some embodiments, crosslinking comprises exposing the silicon adhesive composition to radiation to form a radiation crosslinked silicone adhesive. In some of these embodiments, radiation includes at least one of electron-beam or gamma radiation.

In some embodiments, the present disclosure provides a method of making an adhesive article, the method including coating the primer layer onto the substrate, coating a silicone adhesive composition onto a release liner, crosslinking the silicone adhesive composition to form the silicone adhesive, and laminating the silicone adhesive to the primer layer. In some embodiments, crosslinking comprises exposing the silicon adhesive composition to radiation to form a radiation crosslinked silicone adhesive. In some of these embodiments, radiation includes at least one of electron-beam or gamma radiation.

As the Examples below demonstrate, a primer layer of the present disclosure typically increases the strength of the bond between a silicone adhesive and a substrate. The adhesive strength between the silicone adhesive and the substrate is increased such that it either exceeds the cohesive strength of the silicone adhesive or the adhesive strength between the silicone adhesive and the testing tape (3M Polyester Tape 8403).

Some useful primers can contain reactive functional groups (e.g., epoxy, acrylic, isocyanate, vinyl, or hydrolysable silanes) to form covalent bonds with a substrate and/or an adhesive coated onto the substrate. Still other methods for improving adhesion between a substrate and an adhesive include plasma treatment, corona treatment, or flame treatment of a substrate surface to clean or roughen the surface and/or provide polar functional groups on the surface. In contrast, in the adhesive articles according to and/or made according to the present disclosure, the adhesive strength between the substrate and the adhesive is improved even though the primer layer includingh a polymer having a polyorganosiloxane pendant group P does not contain reactive functional groups to promote interaction with the substrate or the adhesive. An extra step of plasma, corona, or flame treatment of the substrate surface is not required for the adhesive articles disclosed herein.

Furthermore, as shown in the examples below, the disclosed primer layer including a polymer having a polyorganosiloxane pendant group P in some cases is a better primer (that is, provides better adhesion between a silicone adhesive and a substrate) than conventional primers used for silicone adhesives.

EXAMPLES

Unless otherwise noted, all parts, percentages, ratios, etc. in the Examples and the rest of the specification are by weight. Unless otherwise indicated, all other reagents were obtained, or are available from fine chemical vendors such as Sigma-Aldrich Company, St. Louis, Missouri, or may be synthesized by known methods. The following abbreviations are used in this section: min=minutes, s=second, h=hour, g=gram, mg=milligram, kg=kilogram, in=inch, m=meter, centimeter=cm, mm=millimeter, µm=micrometer or micron, ° C.=degrees Celsius, ° F.=degrees Fahrenheit, N=Newton, oz=ounce, Pa=Pascal, MPa=mega Pascal, rpm=revolutions per minute, pph=parts per hundred, psi=pressure per square inch, cc/rev=cubic centimeters per revolution, gsm=grams per square meter, $cm^3$=centimeters cubed, MRad=MegaRad Table 1 (below) lists materials used in the examples and their sources.

TABLE 1

| | Materials |
|---|---|
| DESIGNATION | DESCRIPTION |
| NA443023 | Low density polyethylene/ethylene vinyl acetate, obtained under the trade designation "PETROTHENE NA443023" from LyondellBasell Industries, Houston, TX |
| NA960183 | Low Density Polyethylene, obtained under the trade designation "PETROTHENE NA960183" from LyondellBasell Industries, Houston, TX |
| 5863-90A | Polyurethane, obtained under the trade designation "PELLETHANE-5863-90A" from Lubrizol Corporation, Wickliffe, OH |
| 3SAB primed PET film | One-side primed 2 mil polyester film, obtained under the trade designation "HOSTAPHAN 3 SAB" from Mitsubishi Polyester Film, Greer, SC |
| ARNITEL 3108 | Co-Polyester film, obtained under the trade designation "ARNITEL 3108" from Koninklijke DSM N.V., Heerlen, Netherlands |
| 8010 | Polyester spunlace nonwoven, obtained under the trade designation "SONTARA 8010" from Jacob Holm Group, Basel, Switzerland |
| COTRAN 9700 | Melt-blown polyurethane nonwoven backing, from 3M Company, St. Paul, MN |
| Polyester fabric | Polyester fabric (70/30 Heavy Duty), from Xiaoshan Johnson Cloth Company, Hangzhou, China |
| Foam | 130 Medical Foam on Liner 43-9101-5803-9 from TEGADERM 90616, from 3M Company, St. Paul, MN |
| X-22-176DX | Silicone Diol, obtained under the trade designation "X-22-176DX" from Shin-Etsu Chemical Company, Tokyo, Japan |
| H12MDI | 4,4'-Methylenebis(cyclohexyl) isocyanate, obtained under the trade designation "DESMODUR W" from Covestro, Baytown, TX |
| JEFFAMINE THF 100 | Polyetheramine, obtained under the trade designation "JEFFAMINE THF 100" from Huntsman Corporation, The Woodlands, TX |
| IPA | Isopropyl alcohol, from VWR, Radnor, PA |
| Butyl acrylate | Butyl acrylate, obtained from Dow Chemical, Midland, MI |
| Methyl methacrylate | Methyl methacrylate, from Lucite International, Cordova, TN |
| Iso-octyl acrylate | Iso-octyl acrylate, from 3M Company, St. Paul, MN |
| Tert-butyl amino ethyl methacrylate | Tert-butyl amino ethyl methacrylate, from Kowa American Corporation, New York, NY |
| MEK | Methyl ethyl ketone, from EMD Serono, Billerica, MA |
| DBU | 1,8-Diazabicyclo[5.4.0]undec-7-ene, from Sigma-Aldrich, St. Louis, MO |
| KF-2012 | Silicone Acrylate, obtained under the trade designation "KF-2012" from Shin-Etsu Silicone, Akron, OH |
| Ethyl acetate | Ethyl acetate, obtained from EMD Serono, Billerica, MA |
| VAZO-67 | 2,2'-Azobis(2-methylbutyronitrile), obtained under the trade designation "VAZO-67" from DuPont, Wilmington, DE |
| Polydimethylsiloxane fluid | Polydimethylsiloxane Fluid, obtained under the trade designation "AK 1,000,000" from Wacker Chemical Corp., Adrian, MI |
| MQ 803 TF | Silicone resin powder, obtained under the trade designation "MQ 803 TF" from Wacker Chemical Corp., Adrian, MI |
| OHX-4070 | Polydimethylsiloxane fluid, obtained under the trade designation "OHX-4070" from Xiameter, Midland, MI |

TABLE 1-continued

Materials

| DESIGNATION | DESCRIPTION |
|---|---|
| Polyester Tape | Polyester tape (1-inch-wide), available under the trade designation "3M 8403" from 3M Company, St. Paul, MN |
| Polyolefin-Coated Paper Carrier | Polyolefin-coated paper carrier, obtained from ProAmpac, Neenah, WI |
| MG 7-9900 | Soft Skin Adhesive MG 7-9900 Dow Corning, Midland, MI |
| 1R82001 | Release liner 1R82001, obtained from Siliconature, Godega di Sant' Urbano, Italy |
| MG 7-1010 | Soft Skin Adhesive MG 7-1010 Dow Corning, Midland, MI |

TEST PROCEDURES

Adhesive Anchorage Test

The Adhesive Anchorage bond strength is tested by laminating a section of Polyester Tape (e.g., two to four inches in length) to a cured adhesive surface, prepared as described below and with the release liner removed. Polyester Tape is rolled down onto a cured adhesive surface with two passes of a 2-kilogram roller at 12 inches per minute and then allowed to dwell for 15-20 minutes to provide a test specimen consisting of Polyester Tape laminated onto the cured adhesive surface. The test specimen is mounted with double-coated tape onto the moving plate of an IMASS SP-2300 peel tester (available from IMASS, Inc., Accord, MA). The Polyester Tape is removed from the test specimen at 12 inches per minute at 180° peel angle. The average peel force (average of at least 3 measurements) is reported. The percentage adhesive transfer is visually assessed and recorded, where adhesive transfer is the percent area of the test specimen having no adhesive left on the primed backing after the Polyester Tape is removed from the cured adhesive surface. A primed construction is considered successful if it has minimal (ideally 0%) adhesive transfer from the cured adhesive surface to the Polyester Tape once the test tape had been removed. A primed construction is considered a failure if it shows 50% to 100% adhesive transfer from the cured adhesive surface to the Polyester Tape.

Determination of Inherent Viscosity (IV)

The inherent viscosities ("IV") reported herein were obtained by conventional methods used by those skilled in the art. The IVs were obtained using an AVS 450 viscometer (Lauda Scientific GMBH, Lauda-Konigshofen, Germany) in a water bath at 27° C., to measure the flow time of 10 ml of a polymer 10 solution (0.3 g per deciliter polymer in ethyl acetate). The test procedure followed and the apparatus used are described in detail in Textbook of Polymer Science, F. W. Billmeyer, Wiley-Interscience, Second Edition, 1971, Pages 84 and 85.

Immersion Adhesive Anchorage Test

The Immersion Adhesive Anchorage Test was performed according to the procedure of the Adhesive Anchorage Test above, except that the laminated test specimen consisting of Polyester Tape laminated onto the cured adhesive surface was immersed in tap water at room temperature for one minute before testing. Results of the tests are recorded in Table 5.

SAMPLE PREPARATION

Backing Film Preparation

The LDPE/EVA and LDPE resins were extruded using a Haake single screw extruder (Model: TYP 557-0029, obtained from Thermo Fisher Scientific, Waltham, MA). Example extruder settings for the PETROTHENE NA443023 resin included extruder zone temperatures of 300° F., 350° F., and 400° F.; extrusion die temperature of 400° F.; backup roll temperature of 80° F.; with a nip pressure of 30 psi; screw speeds (rotations per minute) of 120 rpm (for 3 mil (76.2 µm) film) and 130 rpm (for 4 mil (101.6 µm) film); and with a line speed of 15 feet per minute. The LDPE resin PETROTHENE NA960183 extruded at very similar temperature and extruder settings. The films were extruded onto a Polyolefin-Coated Paper Carrier.

The PELLETHANE-5863-90A resin was dried overnight at 150° F. and then extruded using a Haake single screw extruder (Model: TYP 557-0029, obtained from Thermo Fisher Scientific, Waltham, MA). Example extruder settings for the 5863-90A polyurethane resin included extruder zone temperatures of 300° F., 325° F., and 350° F.; extrusion die temperature of 350° F.; backup roll temperature of 150° F.; with a nip pressure of 100 psi; screw speed (rotations per minute) of 77.5 rpm; and with a line speed of 25 feet per minute. The film was extruded at 1 mil (12.7 micrometers (µm)) thickness onto a Polyolefin-Coated Paper Carrier.

Primer Composition Synthesis

The Primer Compositions, i.e., SiPu, SiAcl, and SiAc2, are summarized in Table 2 with preparations described below.

TABLE 2

Primer Compositions

| Name | Descriptions |
|---|---|
| SiPU | Silicone Polyurethane/polyurea in MEK/IPA (1:1): 20 grams X-22-176DX (silicone diol) 36.8 grams H12MDI 143.2 grams JEFFAMINE THF 100 |
| SiAcl | Silicone Acrylate in ethyl acetate: 210 grams butyl acrylate 60 grams methyl methacrylate 30 grams KF-2012 (5k silicone acrylate) |
| SiAc2 | Silicone Acrylate in ethyl acetate/isopropanol (1:1): 132 grams iso-octyl acrylate 72 grams methyl methacrylate 24 grams KF-2012 (5k silicone acrylate) 12 grams tert-butyl amino ethyl methacrylate |
| SPOx | Comparative Examples, 5k SPOx prepared as described in U.S. Pat. No. 9,890,302 (Tse et al.) Example 1 |

Silicone Polyurethane/Polyurea Primer

SiPu

The silicone polyurethane/polyurea polymer was prepared by combining 20 g of a silicone diol X-22-176DX and 125 g of MEK. The material was azeotropically dried by distilling 40 g of MEK. The solution was cooled to 60° C. and 36.8 g of H12MDI and 0.04 g of DBU were added. This solution was stirred at 75° C. for 3 hours and then cooled to 25° C. to provide an isocyanate-terminated prepolymer solution. In a separate reaction vessel, 143.2 g of JEFFAMINE THF 100 and 365 g of IPA were combined. The isocyanate-terminated prepolymer solution was then slowly added to the JEFFAMINE solution, at a rate maintaining a temperature below 3° C. This mixture was stirred at 25° C. for 1 h. The resulting solution obtained was determined to have a 30.5% solids content of silicone polyurethane/polyurea primer. This solution was then diluted to a 5% solids primer coating solution with a 1:1 mix of IPA and MEK.

Silicone Acrylate Primers

SiAc1

The silicone acrylate polymer was prepared by combining 210 grams of butyl acrylate, 60 grams of methyl methacrylate, 30 g of KF-2012, and 367 grams of ethyl acetate. To the mixture was added 2.4 grams of VAZO-67 and the resulting solution was deoxygenated for two minutes with nitrogen.

After heating at 65° C. for 44 hours, a solution was obtained that was determined to have a 44% solids content and an IV of 0.75. This polymer concentrate was then diluted to a 2.5% solids primer coating solution with additional MEK.

SiAc2

The silicone acrylate polymer was prepared by combining 72 grams of methyl methacrylate, 132 grams of iso-octyl acrylate, 24 g of KF-2012 (Shin-Etsu), 12 g of tert-butyl amino ethyl methacrylate, and 360 grams of ethyl acetate. 1.92 grams of Vazo-67 (Dupont) was added and the solution was deoxygenated for 2 minutes with nitrogen. After heating at 65° C. for 46 hours, a solution was obtained that was determined by gravimetric means to have a 39.6% solids content and an inherent viscosity of 0.43. This polymer concentrate was then diluted to a 2.5% solids primer coating solution with additional MEK.

Primer Coating of Backings

Primer solutions were coated onto backings using either a forward style gravure style coating method or Meyer Rod. Target coat weight was 0.1 to 1 gsm and was achieved using a 120 PYM gravure cylinder. Material was coated and then dried in a three-zone oven briefly at 150° F. at a line speed of 30 feet per minute, before being wound up on a core. Primer solution solids were at either 2.5 or 5%. For Meyer Rod coated samples, the drying temperature was 70° C. for 10 minutes in a batch oven.

Adhesive Compositions Preparation

Adhesive 1: AK 1,000,000 polydimethylsiloxane fluid (80 grams) and MQ 803 TF Silicone Resin Powder (20 g) were added to a cup and blended for 90 seconds at 2500 rpm in a mixer (obtained from FlackTek Inc, Landrum, SC, under the trade designation "SPEEDMIXER MODEL DAC 150.1 FV") to form a homogenous mixture. The mixture was notch-bar coated at a thickness of 100 µm onto either a backing (see results in Table 3) or release liner (see results in Table 4) and then was irradiated with an electron beam dose of 3 MRad following the procedure described below under Electron Beam Ionization Treatment of Samples.

Adhesive 2: OHX-4070 polydimethylsiloxane fluid (69 g) and MQ 803 TF Silicone Resin Powder (31 grams) were added to a cup and blended for 90 seconds at 2500 rpm in a SPEEDMIXER MODEL DAC 150.1 FV mixer to form a homogenous blend. The blend was notch-bar coated at a thickness of 100) µm and irradiated with an e-beam dose of 7 MRad following the procedure described below under Electron Beam Ionization Treatment of Samples.

Adhesive 3: MG 7-9900 (50 grams of Part A and 50 grams of part B) was added to a cup and blended for 120 seconds at 1000 rpm in a SPEEDMIXER MODEL DAC 150.1 FV mixer to form a homogenous blend. The blend was notch-bar coated at a thickness of 100 µm on release liner 1R82001 (obtained from Siliconature, Godega di Sant'Urbano, Italy) and cured at 120° C. for ten minutes in a batch oven.

Adhesive 4: MG 7-1010 (50 grams of Part A and 50 grams of part B) was added to a cup and blended for 120 seconds at 1000 rpm in a SPEEDMIXER MODEL DAC 150.1 FV mixer to form a homogenous blend. The blend was notch-bar coated at a thickness of 100 µm on release liner 1R82001 and cured at 120° C. for ten minutes in a batch oven.

Electron Beam Ionization Treatment of Samples

Examples coated with Adhesives 1 and 2 were exposed to ionizing radiation for crosslinking on an electron beam generating apparatus (obtained from Energy Sciences, Inc., Wilmington, MA, under the trade designation "MODEL CB-300") using methods described in U.S. Pat. No. 8,541,481 generally as follows. The samples were attached to a polyethylene terephthalate ("PET") support film to convey them through the nitrogen inerted irradiation chamber of the electron beam generating apparatus. The samples were exposed to radiant energy at 280 kilovolts (kV). Samples were then covered with release liner 1R82001, which is removed before testing.

The compositions of Examples 1-13 (EX1-EX13) and Comparative Examples 1-6 (CE1-CE6) are summarized in Table 3. These samples include an adhesive that is both coated and cured on a backing, where some backings include a primer and other backings do not, as indicated.

The compositions of Examples 14-28 (EX14-EX28) and Comparative Examples 7-22 (CE7-CE22) are summarized in Table 4. These samples include an adhesive that is both coated and cured on a release liner and then laminated to a backing, where some backings include a primer and other backings do not, as indicated.

The electron beam-cured adhesive-coated film specimens were tested using the Adhesive Anchorage Test Method described above. Results of the Adhesive Anchorage Test and visual assessments of the adhesive failure modes are presented in Tables 3 and 4.

TABLE 3

Samples with Adhesive Coated and Cured on Backing

| Example # | Backing | Primer | Adhesive | Average Peel Force (oz/inch) | Adhesive Failure Mode |
|---|---|---|---|---|---|
| CE1 | NA443023 | None | Adhesive 1 | 8.1 | 100% Transfer |
| Ex1 | NA443023 | SiAc2 | Adhesive 1 | 23.4 | 0% Transfer |
| Ex2 | NA443023 | SiAc1 | Adhesive 1 | 21.1 | 0% Transfer |
| Ex3 | NA443023 | SiPU | Adhesive 1 | 26.2 | 30% Transfer |
| CE2 | NA960183 | None | Adhesive 1 | 8.2 | 100% Transfer |
| Ex4 | NA960183 | SiAc1 | Adhesive 1 | 23.4 | 80% Transfer |
| CE3 | 5863-90A | None | Adhesive 1 | 6.6 | 100% Transfer |
| Ex5 | 5863-90A | SiAc2 | Adhesive 1 | 28.7 | 100% Transfer |
| Ex6 | 5863-90A | SiAc1 | Adhesive 1 | 31.6 | 0% Transfer |
| CE4 | 3SAB | None | Adhesive 1 | 13.9 | 100% Transfer |
| Ex7 | 3SAB | SiAc2 | Adhesive 1 | 29.5 | 20% Transfer |
| Ex8 | 3SAB | SiPU | Adhesive 1 | 27.9 | 20% Transfer |
| Ex9 | 3SAB | SiAc1 | Adhesive 1 | 29.4 | 0% Transfer |
| CE5 | 3SAB | None | Adhesive 2 | 12.2 | 100% Transfer |

TABLE 3-continued

Samples with Adhesive Coated and Cured on Backing

| Example # | Backing | Primer | Adhesive | Average Peel Force (oz/inch) | Adhesive Failure Mode |
|---|---|---|---|---|---|
| Ex10 | 3SAB | SiAc2 | Adhesive 2 | 15.0 | 0% Transfer |
| Ex11 | 3SAB | SiPU | Adhesive 2 | 16.6 | 30% Transfer |
| Ex12 | 3SAB | SiAc1 | Adhesive 2 | 15.1 | 0% Transfer |
| CE6 | ARNITEL 3108 | None | Adhesive 1 | 15.2 | 100% Transfer |
| Ex13 | ARNITEL 3108 | SiAc1 | Adhesive 1 | 25.1 | 0% Transfer |

TABLE 4

Examples with Adhesive Coated and Cured on Release Liner

| Example | Backing | Primer | Adhesive | Average Peel Force (oz/inch) | Adhesive Failure Mode |
|---|---|---|---|---|---|
| CE7 | 3SAB | None | Adhesive 3 | N.M. | 100% Transfer |
| Ex14 | 3SAB | SiAc2 | Adhesive 3 | 3.8 | 0% Transfer |
| Ex15 | 3SAB | SiPU | Adhesive 3 | 5.5 | 0% Transfer |
| Ex16 | 3SAB | SiAc1 | Adhesive 3 | 3.1 | 0% Transfer |
| CE8 | 3SAB | None | Adhesive 4 | 10.4 | 100% Transfer |
| Ex17 | 3SAB | SiAc2 | Adhesive 4 | 26.0 | 0% Transfer |
| Ex18 | 3SAB | SiPU | Adhesive 4 | 27.2 | 0% Transfer |
| Ex19 | 3SAB | SiAc1 | Adhesive 4 | 28.3 | 0% Transfer |
| CE9 | 5863-90A | None | Adhesive 4 | 29.5 | 10% Transfer |
| Ex20 | 5863-90A | SiAc2 | Adhesive 4 | 29.3 | 0% Transfer |
| Ex21 | 5863-90A | SiAc1 | Adhesive 4 | 28.0 | 0% Transfer |
| CE10 | 8010 | None | Adhesive 1 | N.M. | 100% Transfer |
| Ex22 | 8010 | SiAc1 | Adhesive 1 | 9.0 | 100% Transfer |
| CE11 | 5863-90A | None | Adhesive 1 | 11.6 | 100% Transfer |
| Ex23 | 5863-90A | SiAc2 | Adhesive 1 | 16.0 | 0% Transfer |
| Ex24 | 5863-90A | SiAc1 | Adhesive 1 | 15.3 | 0% Transfer |
| CE12 | CoTran 9700 | None | Adhesive 1 | 16.6 | 100% Transfer |
| CE13 | CoTran 9700 | None | Adhesive 3 | N.M. | 100% Transfer |
| CE14 | CoTran 9700 | None | Adhesive 4 | 17 | 100% Transfer |
| CE15 | CoTran 9700 | SPOx | Adhesive 1 | 8.9 | 100% Transfer |
| CE16 | CoTran 9700 | SPOx | Adhesive 3 | N.M. | 100% Transfer |
| CE17 | CoTran 9700 | SPOx | Adhesive 4 | 4.3 | 100% Transfer |
| Ex25 | CoTran 9700 | SiPU | Adhesive 4 | 28.9 | 40% Transfer |
| Ex26 | CoTran 9700 | SiAc1 | Adhesive 4 | 23.2 | 100% Transfer |
| CE18 | Polyester fabric | SPOx | Adhesive 1 | N.M. | 100% Transfer |
| CE19 | Polyester fabric | SPOx | Adhesive 3 | N.M. | 100% Transfer |
| CE20 | Polyester fabric | SPOx | Adhesive 4 | N.M. | 100% Transfer |
| Ex27 | Polyester fabric | SiPU | Adhesive 4 | 22.6 | 100% Transfer |
| CE21 | Foam | None | Adhesive 1 | 11.8 | 100% Transfer |
| CE22 | Foam | SPOx | Adhesive 1 | 9.7 | 100% Transfer |
| Ex28 | Foam | SiAc2 | Adhesive 1 | 15 | 40% Transfer |

N.M: not measured;
the adhesives labeled as such did not transfer to the backing from the release liner, hence the Adhesive Anchorage force was not measured.

TABLE 5

Samples Tested with Immersion Adhesive Anchorage Test

| Example # | Backing | Primer | Adhesive | Average peel force in oz/inch | Adhesive failure mode |
|---|---|---|---|---|---|
| CE21 | Foam | None | Adhesive 1 | 8.1 | 100% Transfer |
| CE22 | Foam | SPOx | Adhesive 1 | 8.5 | 100% Transfer |
| Ex28 | Foam | SiAc2 | Adhesive 1 | 12.8 | 40% Transfer |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. An adhesive article comprising:
a substrate;
a primer layer disposed on the substrate; and
a silicone adhesive disposed on the primer layer,
wherein the primer layer comprises a polymer including a polyorganosiloxane pendant group P represented by the formula

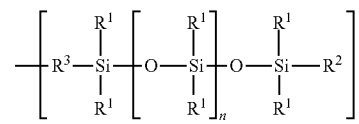

wherein
each $R^1$ is independently an alkyl, haloalkyl, arylalkyl, alkenyl, aryl, or aryl substituted with an alkyl, alkoxy, or halo,
$R^2$ is an alkyl or an alkenyl group;
$R^3$ is an alkylene or an arylalkylene group; and
n is an integer in the range of 1 to 20,
wherein the polymer is a polyurethane polymer comprising a first monomer represented by the formula

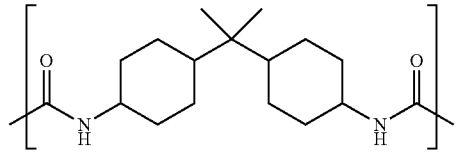

a second monomer represented by the formula

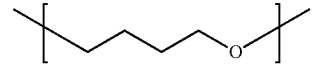

and;
a third monomer represented by the formula

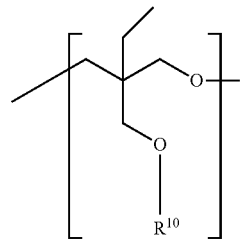

wherein
$R^{10}$ is pendant group P.

2. The adhesive article of claim 1, wherein the polymer is a polyurethane polymer, and wherein the polyurethane polymer has a molecular weight of 10000 g/mol to 100000 g/mol or optionally 20000 g/mol to 50000 g/mol.

3. The adhesive article of claim 1, wherein the substrate comprises a thermoplastic substrate, wherein the substrate is a paper substrate, wherein the substrate is a woven substrate, or wherein the substrate is a nonwoven substrate.

4. The adhesive article of claim 3, wherein the thermoplastic is a polyolefin, a polyester, a polyurethane, or an ethylene-vinyl acetate copolymer.

5. The adhesive article of claim 1, wherein the polymer includes 2 wt. % to 40 wt. %, optionally 2 wt. % to 30 wt. % of a monomer including the polyorganosiloxane pendant group P.

6. The adhesive article of claim 1, wherein the silicone adhesive is a radiation-crosslinked silicone adhesive.

7. The adhesive article of claim 1, wherein the silicone adhesive is a crosslinked poly(diorganosiloxane) comprising silanol, alkyl, or aryl terminal groups or a combination thereof, and wherein alkyl and aryl are optionally halogenated.

8. The adhesive article of claim 1, wherein the adhesive article is a medical article.

9. The adhesive article of claim 8, wherein the medical article is selected from the group consisting of a bandage, a medical tape, a medical drape, an electrode, a dressing, an ostomy pouch, a transdermal drug delivery device, and combinations thereof.

10. A method of making the adhesive article of claim 1, the method comprising:
coating the primer layer onto the substrate;
coating a silicone adhesive composition onto the primer layer; and
crosslinking the silicone adhesive composition to form the silicone adhesive.

11. The method of claim 10, wherein at least one of coating the primer layer or coating the silicone adhesive composition comprises pattern-coating.

12. The method of claim 10, wherein the primer layer improves adhesion between the substrate and the silicone adhesive.

13. The method of claim 10, wherein crosslinking the silicone adhesive composition comprises exposing the silicone adhesive composition to radiation to form the silicone adhesive.

* * * * *